FLOWERING CRABAPPLE TREE

Filed July 22, 1969

INVENTOR
ROBERT C. SIMPSON

BY
Oberlin, Maky, Donnelly & Renner
ATTORNEYS

United States Patent Office

Plant Pat. 3,052
Patented Apr. 20, 1971

3,052
FLOWERING CRABAPPLE TREE

Robert C. Simpson, Vincennes, Ind., assignor to Cole Nursery Company, Inc.

Filed July 22, 1969, Ser. No. 843,862
Int. Cl. A01h 5/03
U.S. Cl. Plt.—34 1 Claim The present invention or discovery relates to a new and distinct variety of ornamental crabapple tree originated by me, having in combination novel blooms and habit of growth, and more particularly consists in a novel variety of Malus, flowering crabapple, having unusual and distinctive characteristics.

My new flowering crabapple tree is a small tree of fast growth having an informal narrow upright growth habit and attractive foliage. It regularly bears an abundance of large double or semi-double dark to purplish red flowers that do not fade.

The novel and distinctive features of this new variety are accordingly considered to be, in combination:

(1) The upright habit of growth.
(2) The rapid rate of growth.
(3) The purplish red color of the young twigs.
(4) The dark red to deep purplish red color of the flower buds.
(5) The strong purplish red color and large size of the double and semi-double flowers.
(6) The cup-shaped form of the flowers and the pendent nature of the flower clusters.
(7) The small size of the dark red fruits which are produced very sparingly and quickly disappear in the turf when they drop.
(8) The extended bloom period.
(9) The early age when the tree comes into bloom.
(10) The hardiness of the tree in the neighborhood of Cleveland, Ohio.

There is a large demand for small ornamental flowering trees for landscape planting, and flowering crabapple trees have been recognized over a long period of time as especially suitable for such purposes. Really good red flowering crabapple trees are, however, very rare, and most of such trees, so called, are in reality purple rather than red flowering. Because of the large size of the double flowers of the tree of the present invention, together with the strong red color of such flowers, and the abundance of bloom, such tree affords a very striking sight where a strong color effect is desired.

My new flowering crabapple tree has been propagated asexually at Circleville, Ohio, by budding and by grafting, and the tree can be very readily propagated in this manner, perpetuating all of its original characteristics. The original parent specimen was a seedling grown by me at Vincennes, Ind., and such original parent specimen was discovered and selected by me in a large plantation of crabapple tree seedlings grown by me from seeds selected from parent trees exhibiting some tendency towards certain of the desired characteristics.

Referring now more particularly to the drawing.

Figure 1:
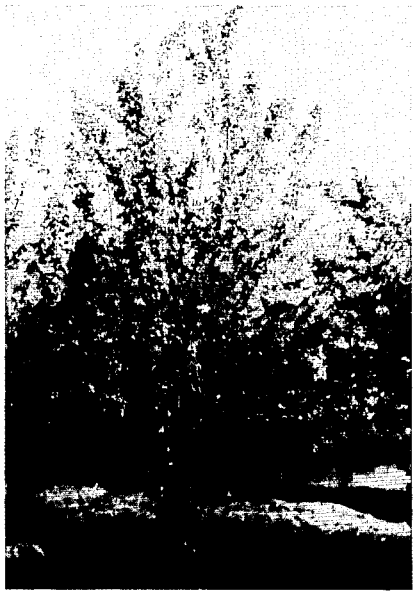
FIG. 1 shows my new flowering crabapple tree in the spring blooming season.
Figure 2:
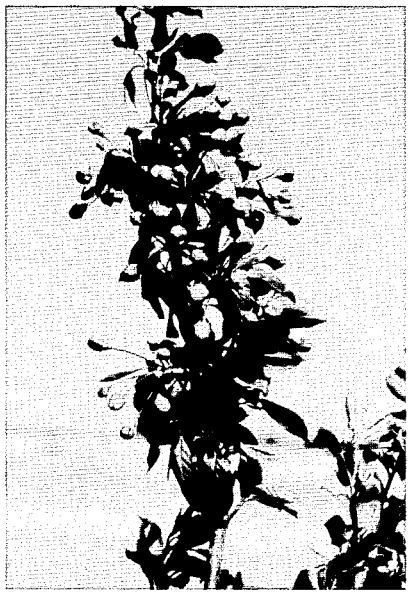
FIG. 2 shows a branchlet of such tree bearing a number of unopened flower buds.
Figure 3:
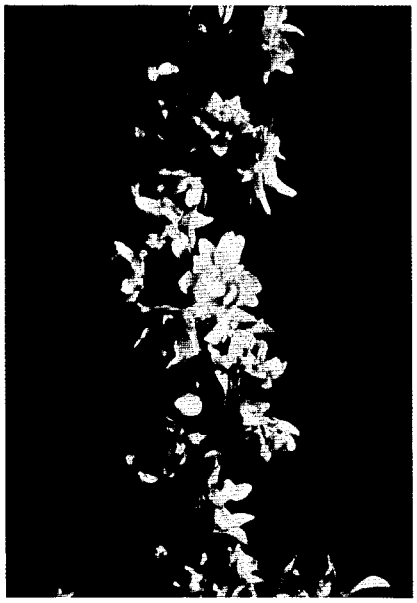
FIG. 3 shows a branchlet of such tree with a number of fully open flowers.
Figure 4:
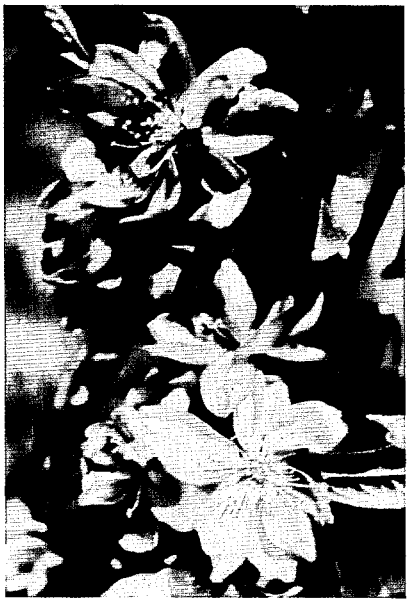
FIG. 4 is a detail view of such flower.

The following is a specific description of such new variety, color terminology in reference to the buds and flowers being in accordance with Nickerson Color Fan:

The original specimen at the Simpson Orchard Company, Inc., Vincennes, Ind. was 8–10 feet in height on Apr. 20, 1968. The specimens propagated therefrom indicate a medium to fast rate of growth (e.g. 18 to 24 inches per year) and an excellent narrow upright habit (e.g. three times as high as it is wide) of semi-informal nature. The side branches are mostly upright and the young twigs are deep purplish red (Nickerson Color Fan 7.5 RP 3/9).

The leaves are broad elliptic to elliptic ovate, 4.5–10 cm. long, slightly toothed, bronzy purple when unfolding, later dark green above with a purplish cast beneath. The petioles are purplish-red.

The flowers are produced abundantly, mostly double with 10–15 petals, 4–7 flowers per cluster and well distributed on the stem. A very small proportion of semi-double flowers also appear. Bloom is produced yearly and the trees normally bloom well even when young. The color of the buds is dark red (Nickerson Color Fan 2.5 R 3/7) to deep purplish red (Nickerson Color Fan 10 RP 3/10), the color holding until the buds are fully opened. The color of the expanded petals is strong purplish red (Nickerson Color Fan 7.5 RP 5/12) with very little color change at maturity (Nickerson Color Fan 7.5 RP 4/11). The flowers tend to hold a cup-shaped form and the flowers tend to be somewhat pendent. The flowers are 3.5–5.0 cm. across, and the flower pedicles are slender, deep reddish purple (Nickerson Color Fan 7.5 RP 3/9), approximately 3.5–4.2 cm. long. The petals are rounded at the tip and broad tapered into a claw at the base, approximately 2.2–3.4 cm. long and 1.0–1.8 cm. wide. The petals are often whitish near the base, the claw being 3.0–4.0 mm. in length. Stamens are medium red to grayish red. The blooming period is medium-late, and flowering duration is long.

Fruits are produced only very sparingly, being somewhat pear-shaped, semi-persistant, dark red in color, and of small size, 1.0–1.5 cm. long and slightly less in width.

I claim:

1. A new and distinct variety of flowering crabapple tree, *Malus cultivar*, having a rapid informal narrow upright growth habit, attractive foliage, an abundance of large double or semi-double, dark to purplish red flowers that do not fade, prominently displayed, an extended bloom period, a minimum production of fruits, and apparent freedom from scab and other diseases.

No references cited.

ROBERT E. BAGWILL, Primary Examiner